(12) United States Patent
Myers et al.

(10) Patent No.: US 8,293,670 B2
(45) Date of Patent: Oct. 23, 2012

(54) PROCESS FOR THE PRODUCTION OF PROPYLENE

(75) Inventors: David N. Myers, Hoffman Estates, IL (US); Daniel N. Myers, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 291 days.

(21) Appl. No.: 12/634,334

(22) Filed: Dec. 9, 2009

(65) Prior Publication Data
US 2011/0137101 A1    Jun. 9, 2011

(51) Int. Cl.
*B01J 38/28* (2006.01)
*C07C 5/333* (2006.01)

(52) U.S. Cl. ........ 502/46; 502/20; 502/34; 502/38; 502/45; 502/56; 585/654; 585/659; 585/660

(58) Field of Classification Search .......... 585/654, 585/660, 659; 502/20, 34, 45, 46, 56, 38
See application file for complete search history.

(56) References Cited

U.S. PATENT DOCUMENTS

| | | | |
|---|---|---|---|
| 3,904,548 A * | 9/1975 | Fagan et al. ............. 502/41 |
| 4,859,643 A | 8/1989 | Sechrist et al. | |
| 4,871,699 A | 10/1989 | Fahrig et al. | |
| 4,951,613 A | 8/1990 | Harandi et al. | |
| 5,030,338 A | 7/1991 | Harandi et al. | |
| 5,220,093 A * | 6/1993 | Gartside et al. ............. 585/661 |
| 5,254,788 A * | 10/1993 | Gartside et al. ............. 585/659 |
| 5,365,006 A | 11/1994 | Serrand | |
| 6,989,346 B2 | 1/2006 | Heineke et al. | |
| 7,087,802 B2 | 8/2006 | Schindler et al. | |
| 7,144,498 B2 | 12/2006 | McCall et al. | |
| 7,276,149 B2 | 10/2007 | Beech et al. | |
| 7,291,961 B2 | 11/2007 | Suzuki et al. | |
| 7,374,660 B2 | 5/2008 | Steffens et al. | |
| 7,381,322 B2 | 6/2008 | Pankaj et al. | |
| 2008/0161624 A1 * | 7/2008 | Glover et al. ............. 585/634 |
| 2009/0159496 A1 | 6/2009 | Hedrick | |

FOREIGN PATENT DOCUMENTS

| | | |
|---|---|---|
| EP | 2072606 A1 | 6/2009 |
| WO | WO 95/27019 | 10/1995 |
| WO | WO 9527019 A1 * | 10/1995 |

OTHER PUBLICATIONS

MacZura, "Aluminum Oxide (Alumina), Calcined, Tabular, and Aluminate Cements" in Kirk-Othmer Encyclopedia of Chemical Technology, John Wiley & Sons, 2001, published on-line Jan. 17, 2003.*
PCT International Search Report and Written Opinion, for PCT/US2010/049746, mailing date Jun. 16, 2011.
Gascon, J. et al.; A Two-Zone Fluidized Bed Reactor for Catalytic Propane Dehydrogenation, Chemical Engineering Journal 106 (2005) p. 91-96.
Stitt, E.H. et al.; Modelling Propane Dehydrogenation in a Rotating Monolith Reactor, Catalysis Today 69 (2001) p. 217-226.
Zhang, X., et al.; Modeling of Coke Burning-off Regeneration for Coked Propane Dehydrogenation Catalyst, CIESC Journal, vol. 60, No. 1, Jan. 2009, p. 163-167 (English abstract).

* cited by examiner

*Primary Examiner* — In Suk Bullock
*Assistant Examiner* — Bradley Etherton
(74) *Attorney, Agent, or Firm* — Arthur E Gooding

(57) ABSTRACT

A process for catalyst regeneration is presented. The process regenerates a catalyst in a paraffin dehydrogenation process, where the reaction is endothermic. The regeneration process provides the heat for the process through heating the catalyst and removes the need for a charge heater to the dehydrogenation reactor, which in turn eliminates high temperature thermal residence time which eliminates thermal cracking of the feed and improves the overall product selectivity. In addition, plot area, equipment costs and operating complexity are reduced.

19 Claims, 2 Drawing Sheets

PROCESS FOR THE PRODUCTION OF PROPYLENE

FIELD OF THE INVENTION

The present invention relates to the production of light olefins from paraffins. Specifically, the invention is directed at propane dehydrogenation in the production of propylene.

BACKGROUND OF THE INVENTION

Continuous catalytic conversion processes are common in the refining and petrochemical industry. The fluidized catalyst cracking of hydrocarbons is an important process for the production of lighter hydrocarbon components, and as such, it is an important process for the production of propylene. The fluidized catalytic cracking process continuously circulates a fluidized catalyst between a reactor and a regenerator.

Another route for the production of propylene can be obtained by the dehydrogenation of propane through catalytic dehydrogenation. The dehydrogenation catalysts generally comprise noble metal catalysts on acidic supports, such as alumina, or silica alumina, or zeolitic materials. However, the reaction is strongly endothermic, and requires a high temperature for the reaction to proceed at a satisfactory rate. The process also leads to coking of the catalyst, and deactivates the catalyst. The catalyst therefore needs to be regenerated on a regular basis after relatively short periods of operation, or residence, in the dehydrogenation reactor.

The production of propylene through dehydrogenation is an endothermic process and requires a substantial amount of additional heating to allow the process to proceed. The use of fuel fired charge heaters provides additional heat to the dehydrogenation reactors, but also results in problems such as fouling or coking of the charge heater tubes that can reduce the on-stream availability of the plant and increase the maintenance costs. Also, there is a loss of propylene yield that occurs due to non-selective cracking due to the thermal residence time in the heater and heater transfer line to the reactor.

SUMMARY OF THE INVENTION

The present invention provides a process for producing propylene through a dehydrogenation reactor, and eliminates the need for a charge heater. The process comprises recirculating catalyst in a dehydrogenation process wherein the partially coked catalyst is passed from the dehydrogenation reactor to a catalyst regenerator. The catalyst is regenerated and heated to a temperature of at least 575° C. (1067° F.). The catalyst and regeneration gases pass through the regenerator at a velocity of at least 1.2 m/s (4 ft/sec) in the regenerator. The regeneration gases burn off coke deposited on the catalyst. In addition, supplemental fuel is added to continue heating the catalyst to a temperature sufficient to provide the energy for the dehydrogenation reaction.

In one embodiment, the invention comprises a process for the dehydrogenation of paraffins in the C3 to C4 range. A paraffin feedstream is passed to a dehydrogenation reactor, with the paraffins reacting in the reactor at reaction conditions to generate an olefin rich product stream. A heated dehydrogenation catalyst is passed to the reactor to provide the heat for the endothermic reaction and to maintain the reaction temperature to the desired value. The catalyst passes through the reactor and is separated from the olefin product stream and passed to a regeneration unit. The catalyst and regeneration gases are mixed in the regenerator and pass through the regenerator at a velocity of at least 1.2 m/s, thereby generating a heated regenerated catalyst stream. The catalyst is regenerated and heated to a temperature of at least 575° C. (1067° F.). The regenerated catalyst is then passed back to the dehydrogenation reactor.

Other objects, advantages and applications of the present invention will become apparent to those skilled in the art from the following detailed description.

DETAILED DESCRIPTION OF THE INVENTION

A process for the dehydrogenation of paraffins can be carried out through a fluidized bed system. However, due to the highly endothermic nature of the reaction, a substantial amount of heat is needed to be added to the reaction to maintain the reaction at a temperature sufficient for the reaction to proceed at a satisfactory rate. The usual practice of a fluidized bed requiring additional heat is to add a charge heater. The present invention has found that this reaction can be carried out without the added equipment of a charge heater. The invention provides for a simpler operation, fewer equipment pieces, a reduced plot area and improvement of overall reaction selectivity to desired product.

Figure 1:
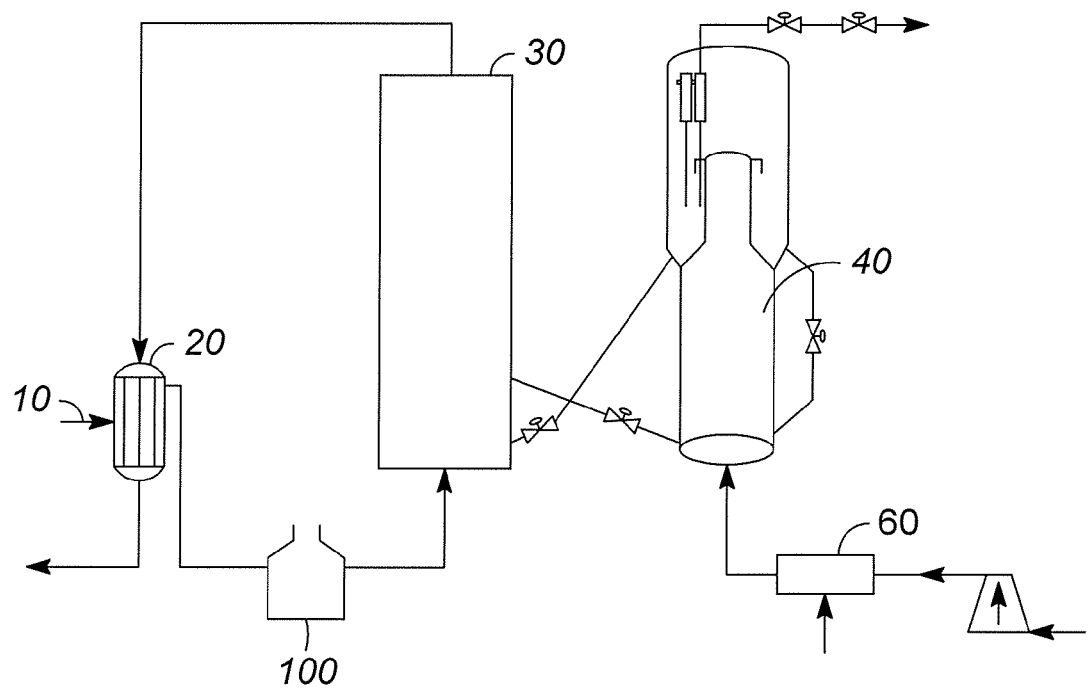
FIG. 1 is a diagram of a fluidized bed propane dehydrogenation process with a charge heater.

Typically, catalytic dehydrogenation processes require a charge heater. As shown in FIG. 1, a paraffin feed 10 is preheated with a heat exchanger 20 to recover heat from the product. The feed is further heated with a charge heater 100 to elevate the feed temperature to the reaction temperature to the desired temperature for the dehydrogenation reaction. The high temperatures in the charge heater 100 can lead to fouling or coking in the heating tubes. In catalyst dehydrogenation processes which use a fluidized bed system, a portion of the heat necessary for the reaction is supplied by the circulating catalyst in the process. However, there is an insufficient amount of heat without the charge heater to maintain the reaction temperature for the dehydrogenation process. Currently, the operation of a propane dehydrogenation reactor includes a charge heater to supply the necessary heat to the dehydrogenation reactor. However, the charge heater also has a potential for fouling or coking in the heating tubes and undesirable thermal residence time which contributes to non-selective thermal cracking of the feedstock.

Elimination of the charge heater 100 for the dehydrogenation reactor 30 results in about a 30 wt % increase of the catalyst circulation rate. This also eliminates the thermal residence time of the hydrocarbon feed from the charge heater outlet to the reactor, and in this case, the propane feed. Eliminating high temperature thermal residence time minimizes thermal cracking of the feed, and improves the overall product selectivity. The elimination of the undesirable thermal residence time increases propane selectivity to propylene by up to about 5 wt %.

The regenerator needs to be operated to provide sufficient mixing of the catalyst particles, and to have sufficient particle to particle contact to prevent excessive localized heating of the particles. The catalyst can be dense, but with a small enough particle size, such that the catalyst is still lifted and carried through the regenerator. The particle sizes are in the 10 to 100 micrometer size range with an average particle size of about 75 micrometers. The combustion gas and catalyst velocity is greater than 0.9 m/s (3 ft/sec), with a preferred velocity of greater than 1.2 m/s (4 ft/sec). The regenerator regenerates the catalyst by combusting the carbon, in the form of coke, deposited on the catalyst during the dehydrogenation process. The regenerator comprises a combustion zone where the carbon on the catalyst reacts with a heated gas comprising oxygen to convert the carbon to $CO_2$. The heated gas will generally have a relatively low oxygen content of less than 10% by volume.

It was discovered that by the addition of heat to the regenerator, the necessary heat can be supplied without a charge heater, and can remove the potential for fouling or coking in the heating tubes. The process is performed by adding the heat to the catalyst in the regenerator, to supply the necessary heat for the reactor's energy needs. During the regeneration process, coke buildup on the catalyst is combusted to regenerate the catalyst, but there is insufficient coke produced in the dehydrogenation reactor to provide the necessary heat for the dehydrogenation reactor's energy needs. The coke production onto the catalyst from the dehydrogenation process provides only about 25 to 33% of the reactor's energy needs. Additional heat can be supplied with additional fuel gas to the regenerator. The catalyst needs to be heated without allowing for excessive localized temperatures which can damage the catalyst through thermal deactivation.

Industry experience with burning auxiliary fuel in bubbling bed FCC regenerators indicates catalyst deactivation occurs due to high localized temperatures. However, the experience is limited to burning torch oil which is FCC feed atomized with steam. The bubbling bed regenerators operate at velocities of approximately 0.9 m/s (3 ft/sec) and with catalyst and gas densities of approximately 0.56 g/cc (35 lb/ft3). By operating a combuster style regenerator with a velocity of between 1.1 m/s and 2.5 m/s (3.5 to 8 ft/sec), and preferably at approximately 1.5 m/s, it was discovered that there was no appreciable thermal damage, or deactivation, of the catalyst. This substantiates that a high rate of mixing, due to a high velocity of the catalyst and regeneration gas in the regenerator, provides a high rate of particle to particle heat transfer and minimizes excessive heating of individual catalyst particles. This discovery provided the technical basis for the invention which adds the needed heat for dehydrogenation to the fluidized circulating catalyst.

The present invention provides a process for sufficiently heating the catalyst during the regeneration stage, and returning the catalyst to the dehydrogenation reactor, allowing for the removal of the charge heater. This removes several problems associated with the charge heater, such as fouling or coking in the heater tubes, and simplifies operation of the dehydrogenation process and removes undesirable thermal residence time. The invention is a process for regenerating catalyst in a propane dehydrogenation process, comprising passing partially coked dehydrogenation catalyst to a regenerator. Adding auxiliary fuel to the regenerator, where the auxiliary fuel is combusted in the regenerator. The partially coked catalyst is regenerated, and heated to a temperature of at least 575° C. (1067° F.). The regeneration process includes combusting coke that has accumulated on the catalyst during the dehydrogenation process. The catalyst in the regenerator is passed through the regenerator at a velocity, including mixing of the catalyst with the regeneration gases, of at least 1.2 m/s (4 ft/sec), thereby producing a regenerated catalyst stream. The catalyst is maintained in a well mixed condition; additional fuel gas is added and the catalyst and gas mixture travel at a velocity sufficient to prevent localized overheating of the catalyst. The heated regenerated catalyst provides the necessary energy for the dehydrogenation process.

The temperature of the regenerated catalyst is preferably heated to at least 625° C. (1160° F.), and more preferably heated to a temperature between 650° C. and 790° C. (1200 to 1450° F.), and most preferably the catalyst is heated to a temperature of at least 700° C. (1292° F.).

A hot regeneration gas is passed to the regenerator to heat and regenerate the catalyst as the catalyst is carried through the regenerator by the gas. Catalyst can be recirculated within the regenerator to obtain a controlled density within the combustor. The gas velocity is preferably maintained at 1.5 m/s (5 ft/sec) for mixing. Catalyst is recirculated from the upper vessel to the combustor to maintain density. The catalyst is recirculated to provide a density of the combined gas and catalyst between 0.06 g/cc and 0.38 g/cc (4 and 24 lb/ft$^3$) in the regenerator. Preferably the density of the combined gas and catalyst is between 0.08 g/cc and 0.30 g/cc (5 and 19 lb/ft$^3$) in the regenerator. This provides for mixing and sufficient distribution of the heat to prevent localized overheating of the catalyst. The gas velocity is preferably maintained at 1.5 m/s (5 ft/sec) for mixing. The catalyst is recirculated to provide a density of the gas and catalyst between 0.14 g/cc and 0.24 g/cc (9 and 15 lb/ft$^3$) in the regenerator, and a more preferred amount to provide a density between 0.16 g/cc and 0.20 g/cc (10 and 12.5 lb/ft$^3$).

In an alternate embodiment, the operation can be performed with a combined flowing gas and catalyst density of less than 0.38 g/cc (24 lb/ft3), with a preferred flowing gas and density in the regenerator between 0.14 g/cc and 0.20 g/cc (9 and 12.5 lb/ft3).

The present invention is utilizing the regenerated catalyst for providing the necessary heat for the dehydrogenation process. The catalyst is heated in the regenerator, and the heated and regenerated catalyst is passed to the dehydrogenation reactor, but cools during the dehydrogenation process. In order to provide sufficient heat, the catalyst is recirculated at a greater rate than for the normal operation of a dehydrogenation process with a charge heater. The recirculation rate of the catalyst is at a rate between 15% and 45% greater than the circulation rate for a fluidized process reaction system with a charge heater. The recirculation rate is preferred to be approximately 30% more than the recirculation rate for a fluidized catalyst dehydrogenation process reaction system with a charge heater. The higher circulation rate maintains a higher average catalyst activity in the fluidized bed dehydrogenation process.

One embodiment of the invention is a process for the dehydrogenation of paraffins in the C3 to C4 range, propane and butanes, comprising passing a paraffin feedstream to a dehydrogenation reactor. Passing a dehydrogenation catalyst to the dehydrogenation reactor, and reacting the paraffin in the reactor at reaction conditions thereby generating an olefin rich product stream. The process further includes separating the catalyst from the olefin rich product stream and passing the catalyst to a regeneration unit. The catalyst is regenerated in the regenerator and heated to a temperature of at least 575° C. (1067° F.), wherein the catalyst passes through the regeneration section of the regenerator at a velocity of at least 1.2 m/s, thereby producing a heated regenerated catalyst stream. A fuel is fed to the regenerator for providing the heat to regenerate the catalyst in the regenerator. Additional fuel is added to provide additional heat needed to raise the temperature of the catalyst, when the charge heater is removed from the dehydrogenation reactor feed. The regenerator is preferably a combustion style regenerator, where the fuel combusts within the regenerator. The heated and regenerated catalyst is then passed back to the dehydrogenation reactor.

In a broad sense, any fuel that has little or no metals can be used, including gas, oil, diesel, naphtha, or other low metal oils, or a combination of gas and liquid fuels can be fed to the regenerator. The fuel is atomized or vaporized as the fuel is fed to the regenerator, and then combusts to heat the catalyst for regeneration. A gas stream can be used in place of steam for the atomization of liquid fuels to be combusted.

The spontaneous ignition temperature for the fuel gas is 538° C. (1000° F.), and the hot catalyst provides the temperature source for the ignition. The fuel gas can be fed through fuel gas nozzles that are similar in design to FCC Unit torch oil nozzles. Fuel gas can also be used as a vaporizing, or atomizing, medium for liquid fuels to create a fuel vapor or fuel with atomized drops to feed into the regenerator.

At start up, the catalyst needs to be heated to start the initial regeneration process, and can be heated with hot air. This can be provided with a direct fired air heater to a temperature of approximately 455° C. to 705° C. (850° F. to 1300° F.), preferably 593° C. (1100° F.) to 650° C. (1200° F.). After the startup, fuel gas is added to the regenerator, where spontaneous combustion provides for the necessary heating to initiate the process of burning off coke from the catalyst and regenerating the catalyst, and with the burning coke providing up to 25 to 33% of the heat needed for the regeneration process.

The amount of fuel fed to the regenerator for combustion is dependent on the coke on catalyst, catalyst circulation rate, the regenerator air feed rate, the regenerator temperature, and the fuel gas composition.

Calculations were performed to determine the amount of fuel needed. The basis for the calculations included an air temperature from the main air blower of 232° C. (450° F.). From the calculations, heating the air to within the direct fired air heater outlet temperature limitation can provide approximately 30% of the heat requirement. If more than about 30% of the regenerator heat requirements are to come from auxiliary fuel, then the fuel needs to be added to directly combust in the regenerator. Without the invention of continuous direct combustion of auxiliary fuel in the regenerator, additional air flow rate would be required to the direct fired air heater to allow for the heat requirement to be met while staying within the outlet temperature limitation of the direct fired air heater. This additional air requirement would require a larger and more costly regeneration system. As noted previously, the coke production onto the catalyst from the dehydrogenation process provides only about 20 to 33% of the reactor's energy needs. Additional heat can be supplied with additional fuel gas to the regenerator. As shown in FIG. 1, fuel is only added to the direct fired air heater 60 to provide the heat needed for the reaction system. For propane dehydrogenation, where there is low coke formation, more than half of the regenerator heat requirements will need to come from the combustion of auxiliary fuel.

Figure 2:
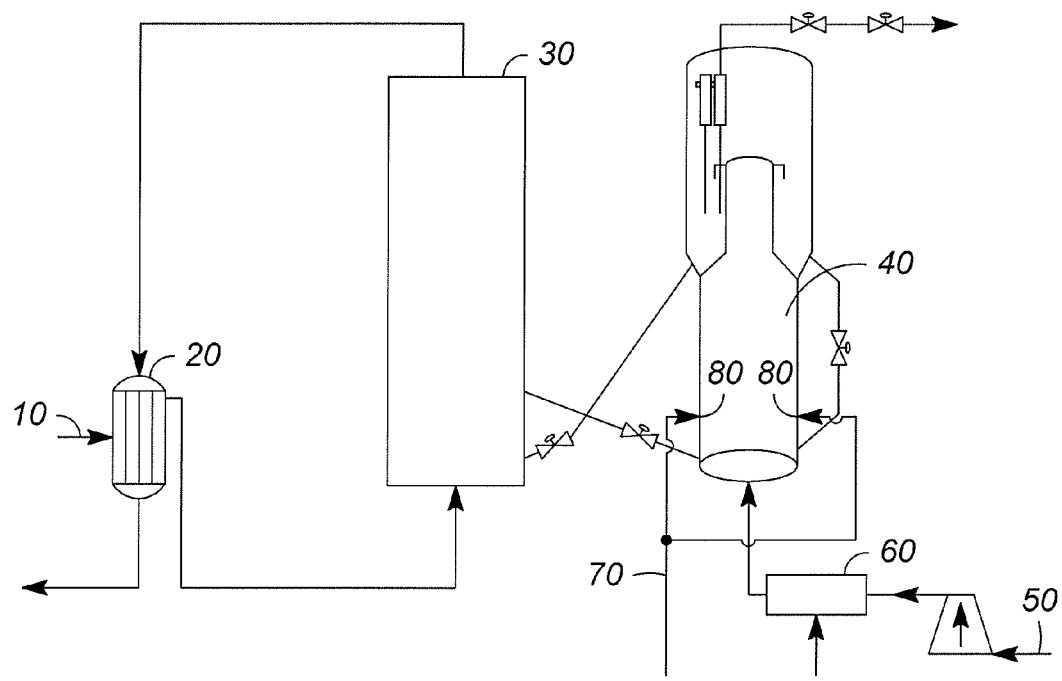
FIG. 2 is a diagram of a fluidized bed propane dehydrogenation process without the charge heater.

The propane dehydrogenation process of the present invention is shown in FIG. 2. A paraffin rich hydrocarbon feed stream 10 is preheated in a heat exchanger 20 before passing to a dehydrogenation reactor 30. The paraffins react with the catalyst, passing upward through the reactor 30. The catalyst is heated to provide the necessary heat for driving the dehydrogenation reaction to generate olefins. The endothermic reaction cools the catalyst, and the catalyst is continuously replaced with fresh heated catalyst. To maintain sufficient reaction temperature, the catalyst is circulated through the reactor at a greater circulation rate than a design with a charge heater. The catalyst is separated from the effluent stream and passed to a regeneration unit 40. Air 50 is compressed and passed to the regenerator 40. During start up, a direct fired air heater 60 is used to provide the initial heat. The air burns off the coke from the catalyst generated during the dehydrogenation reaction. The combustion of the coke provides a portion of the energy for heating the catalyst. The catalyst needs additional heat to raise the catalyst temperature sufficiently before returning the catalyst to the dehydrogenation reactor 30. The additional heat is supplied by combusting an auxiliary fuel 70 that is fed to auxiliary fuel burners 80. The fuel burners 80 add the necessary heat to sufficiently raise the catalyst temperature. The regenerator is sized for a regeneration gas velocity of approximately 1.1 to 2.5 m/s (3.5 to 8 ft/sec), and preferably about 1.5 m/s (5 ft/sec), and the catalyst is circulated at a sufficient rate to insure sufficient turbulence and mixing of the catalyst. This prevents localized overheating of individual catalyst particles, which can deactivate the catalyst.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for regenerating a catalyst in a propane dehydrogenation process comprising:
    passing dehydrogenation catalyst having coke deposited on the catalyst to a regenerator;
    passing auxiliary fuel to the regenerator, wherein the auxiliary fuel produces 67% to 75% of the energy needs of a dehydrogenation reactor; and
    heating the dehydrogenation catalyst in the regenerator to at least 575° C., wherein the catalyst is mixed with a regeneration gas such that the velocity of the mixture of gas and catalyst is at least between 1.1 m/s and 1.5 m/s in the regenerator, thereby producing a regenerated catalyst stream, and wherein the catalyst is recirculated within the regenerator to provide a density of the gas and catalyst in the regenerator of between 0.06 g/cc and 0.38 g/cc.

2. The process of claim 1 wherein the catalyst is heated to a temperature of at least 625° C.

3. The process of claim 2 wherein the catalyst is heated to a temperature between 650° C. and 790° C.

4. The process of claim 3 wherein the catalyst is heated to a temperature of at least 700° C.

5. The process of claim 1 wherein the velocity is between 1.1 m/s and 1.5 m/s and the catalyst is recirculated within the regenerator to provide a density of the gas and catalyst in the regenerator of between 0.14 g/cc and 0.24 g/cc.

6. The process of claim 5 wherein the velocity is between 1.1 m/s and 1.5 m/s and the catalyst is recirculated within the regenerator to provide a density of the gas and catalyst in the regenerator of between 0.16 g/cc and 0.20 g/cc.

7. The process of claim 1 wherein the flowing gas and catalyst has a density in the combustion zone of the regenerator of less than 0.30 g/cc.

8. The process of claim 7 wherein the flowing gas and catalyst has a density in the combustion zone of the regenerator of between 0.14 g/cc and 0.20 g/cc.

9. The process of claim 1 wherein the catalyst is recirculated between the reactor and regenerator at a rate between 15% and 45% greater than for a fluidized catalyst dehydrogenation process reaction system with a charge heater.

10. The process of claim 1 further comprising passing the regenerated catalyst stream to a dehydrogenation reactor.

11. The process of claim 1 wherein the regenerator is a combustor style regenerator with a velocity between 1.1 m/s and 2.5 m/s.

12. A process for dehydrogenation of paraffins in the C3 to C4 range comprising:
  passing a paraffin feedstream to a dehydrogenation reactor;
  passing a dehydrogenation catalyst to the dehydrogenation reactor;
  reacting the paraffin in the reactor at reaction conditions thereby generating an olefin rich prodcut stream;
  separating the catalyst from the olefin rich product stream and passing the catalyst to a regeneration unit;
  passing auxiliary fuel to the regenerator, wherein the auxiliary fuel provides 67% to 75% of the energy needs of the dehydrogenation reactor;
  heating the dehydrogenation catalyst in the regenerator to at least 575° C., wherein the catalyst is mixed with a combustion gas such that the velocity of the catalyst is between 1.2 m/s and 1.5 m/s in the regenerator, and wherein the catalyst is recirculated within the regenerator, thereby producing a heated regenerated catalyst stream; and
  passing the heated regenerated catalyst to the dehydrogenation reactor.

13. The process of claim 12 wherein the catalyst is heated to a temperature between 650° C. and 790° C.

14. The process of claim 13 wherein the catalyst is heated to a temperature of at least 700° C.

15. The process of claim 12 wherein the velocity is between 1.2 m/s and 1.5 m/s and the catalyst is recirculated to provide a density of the gas and catalyst in the regenerator of between 0.06 g/cc and 0.38 g/cc.

16. The process of claim 15 wherein the velocity is between 1.2 m/s and 1.5 m/s and the catalyst is recirculated to provide a density of the gas and catalyst in the regenerator of between 0.14 g/cc and 0.24 g/cc.

17. The process of claim 12 wherein the flowing gas and catalyst has a density in the combustion zone of the regenerator of less than 0.30 g/cc.

18. The process of claim 17 wherein the flowing gas and catalyst has a density in the combustion zone of the regenerator of between 0.14 g/cc and 0.20 g/cc.

19. The process of claim 12 wherein the regenerator is a combustor style regenerator with a velocity about 1.5 m/s.

* * * * *